United States Patent [19]
Cooke et al.

[11] 3,963,717
[45] June 15, 1976

[54] TRICYCLIC FURO-QUINAZOLINONES
[75] Inventors: George A. Cooke, Denville; William J. Houlihan, Mount Lakes, both of N.J.
[73] Assignee: Sandoz, Inc., E. Hanover, N.J.
[22] Filed: Mar. 10, 1975
[21] Appl. No.: 556,574

[52] U.S. Cl.................. 260/251 QB; 260/346.2 R; 424/251
[51] Int. Cl.² ..................................... C07D 491/04
[58] Field of Search............................. 260/251 QB

[56] References Cited
UNITED STATES PATENTS
3,748,342   7/1973   Cooke et al.................. 260/332.3 P

*Primary Examiner*—Raymond V. Rush
*Attorney, Agent, or Firm*—Gerald D. Sharkin; Richard E. Vila

[57] ABSTRACT

Anti-inflammatories and analgesics of the formula

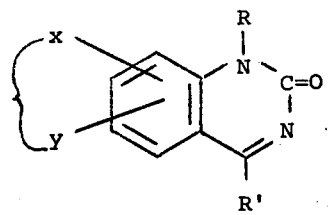

wherein
  x̄ȳ is —OCH$_2$CH$_2$— or —CH$_2$CH$_2$O—,
  R is lower alkyl, allyl or cycloalkylalkyl and
  R' is phenyl or phenyl monosubstituted by halo, alkyl, alkoxy or trifluoromethyl,
are prepared by oxidation of the corresponding dihydro intermediates.

88 Claims, No Drawings

TRICYCLIC FURO-QUINAZOLINONES

The present invention relates to substituted tricyclic compounds which are furo[3,2]quinazolinones and furo[2,3] quinazolinones to their preparation and intermediates useful in their preparation and to pharmaceutical compositions and methods for utilizing the pharmacological activity of such compounds.

The compounds of the present invention may be represented by the following structural formula I:

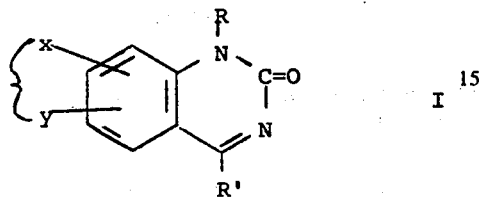

I wherein $\widetilde{x\,y}$ is —OCH$_2$CH$_2$— or —CH$_2$CH$_2$O—,

R is alkyl of 1 to 6 carbon atoms, allyl, methallyl or cycloalkylalkyl of 4 to 8 carbon atoms in which the cycloalkyl portion is of 3 to 6 carbon atoms and the alkyl portion is of 1 to 2 carbon atoms, R' is

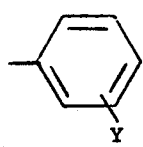

and

Y is hydrogen, halo of atomic weight of from 18 to 36, i.e., fluoro or chloro, alkyl of 1 to 4 carbon atoms, alkoxy of 1 to 4 carbon atoms or trifluoromethyl.

The compounds of the formula I may be prepared by oxidizing a compound of the formula II:

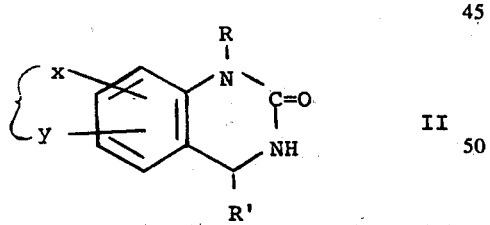

II in which $\widetilde{x\,y}$, R and R' are as above defined, in an inert solvent.

The preparation of compounds I from compounds II may be carried out by oxidizing a compound II in an inert organic solvent at temperatures in the range of from 0°C. to 120°C., preferably 15°C. to 100°C. Suitable oxidizing agents which may be employed are of known type for converting a cyclic amino moiety to an amide moiety. Representative of such oxidizing agents are the alkali metal permanganates, such as sodium or potassium permanganates, manganese dioxide and mercuric acetate. The permanganates are the preferred oxidizing agents. Suitable solvents are of known type and include, for example, methylene chloride, the lower alkanols such as methanol and ethanol, the aromatic solvents such as benzene and the ethers including the cyclic ethers such as dioxane.

The compounds of the formula I may be considered as involving the following six classes of compounds of the structural formulae IA, IB, IC, ID, IE and IF:

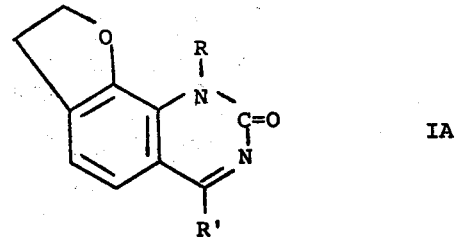

IA

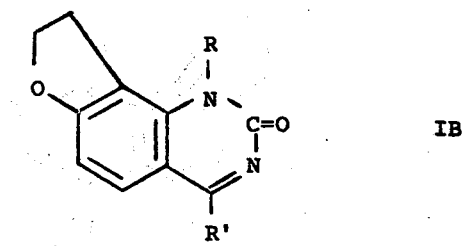

IB

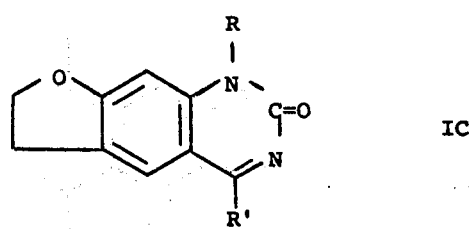

IC

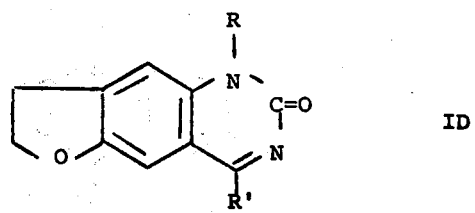

ID

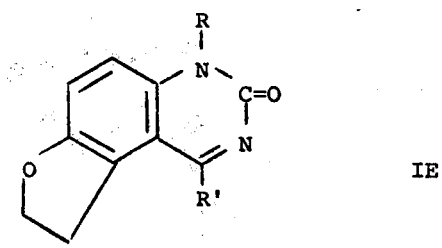

IE

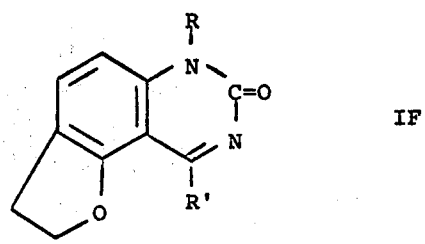

IF in which R and R' are as defined.

As evident from the above description each of the compounds IA, IB, IC, ID, IE and IF is prepared by oxidizing respectively a compound of the following formulae IIA, IIB, IIC, IID, IIE and IIF:

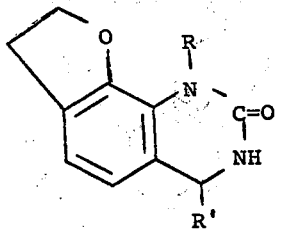 IIA

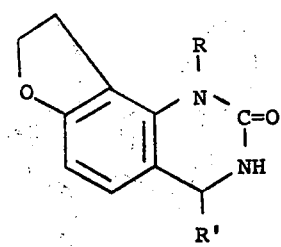 IIB

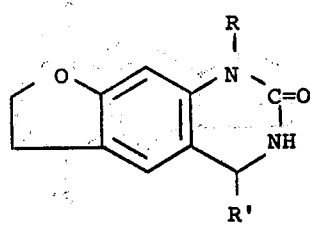 IIC

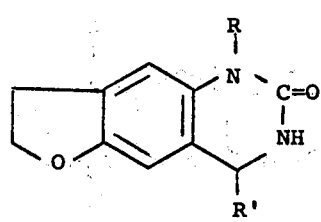 IID

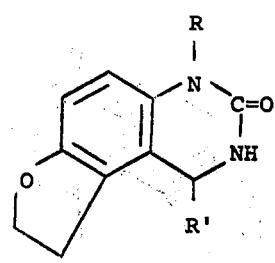 IIE

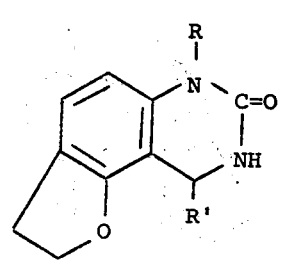 IIF in which R and R' are as above defined.

The compounds of the formula IIA may be obtained in a Step A reaction by reacting a compound of the formula IIIA:

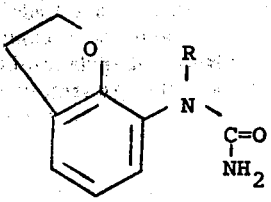 IIIA in which R is as defined, with a compound of the formula IV:

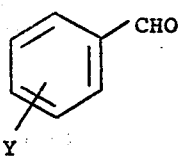 IV in which Y is as defined.

The compounds of the formula IIB may be obtained in a Step B reaction by reacting a compound of the formula IIIB:

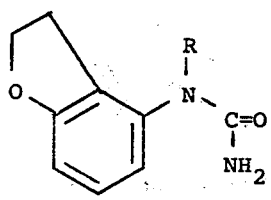 IIIB in which R is as defined, with a compound of the formula IV as given above.

The compounds of the formula IIC and IIF may be obtained in a Step CF reaction by reacting a compound of the formula IIICF

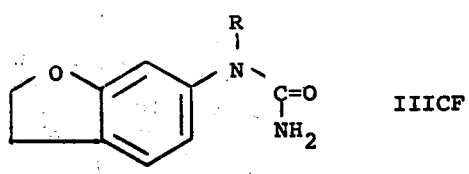 IIICF in which R is as defined, with a compound of the formula IV as given above.

The compounds of the formulae IID and IIE may be obtained in a Step DE reaction by reacting a compound of the formula IIIDE:

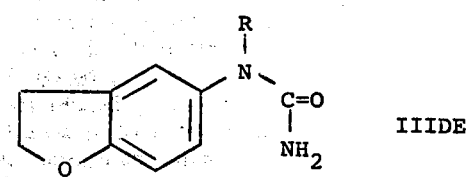 IIIDE in which R is as defined, with a compound of the formula IV as given above.

The reactions of Steps A, B, CF and DE are carried out at temperatures in the range of from 30°C. to 120°C., preferably 50°C. to 100°C. The reactions are suitably carried out in the presence of an acid which serves as both a catalyst and dehydrating agent. Suitable such acids include the inorganic mineral acids such as hydrochloric acid (hydrogen chloride in an aromatic solvent) or an organic acid such as trifluoroacetic acid or an alkylsulfonic acid, p-toluenesulfonic acid and methanesulfonic acid, preferably the latter. The amount of acid is desirably controlled at a minor amount not substantially exceeding about one molar equivalent based on the compound of the formula III-(IIIA, IIIB, IIICF and IIIDE) and is desirably a minor catalytic amount between 0.005 to 0.5 molar equivalent based on the urea of the formula III. The reactions are conducted under anhydrous or substantially anhydrous conditions. The reactions are also conveniently carried out in an organic solvent which may be any of several conventional organic solvents providing an inert reaction medium, preferably an aromatic solvent such as benzene, toluene and the like. Reaction times are typically between 1 and 50 hours. The reaction products of the Step A, B, CF and DE reactions may be isolated and recovered by working up by established procedures. The Step CF and Step DE reactions produce mixtures of the compounds IIC and IIF and the compounds IID and IIE, respectively, and the individual products of the formula II may be separated and recovered from such mixtures by conventional procedures, e.g. column chromatography.

The compounds of the formula IIIA, IIIB, IIICF and IIIDE are referred to herein collectively as the compounds of the formula III which may be represented by the structure:

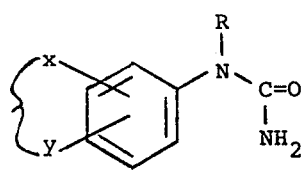

wherein $\overset{\frown}{xy}$ and R are as defined.

The compounds of the formula III are preferably prepared by reacting a compound of the formula V:

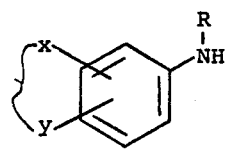

in which $\overset{\frown}{xy}$ and R are as defined, with isocyanic acid which is desirably provided in a conventional manner by preparation in-situ from an alkali metal isocyanate and a suitable acid such as a lower aliphatic carboxylic acid, preferably acetic acid. The reaction is suitably carried out at temperatures of from 10°C. to 50°C. and in an organic solvent medium which is conveniently a lower aliphatic carboxylic acid such as excess acetic acid.

The compounds of formula V may be suitably prepared from known materials by established procedures. A preferred method of preparation of compounds V employs as starting material a compound of formula VI:

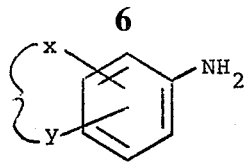

in which $\overset{\frown}{xy}$ is as defined, and involves subjecting said compound VI to known type protection reactions such as to reaction with a trialkylorthoformate followed by treatment with a strong acid such as sulfuric acid; or to tosylation, alkylation and detosylation, all in a manner known per se. It will be noted that compounds V in which R is a cycloalkyl or a branched hydrocarbon with the branching occurring on the carbon atom to be attached to amino nitrogen, e.g., R is isopropyl, may be most conveniently and preferably prepared by reacting directly compound VI with the appropriate alkyl halide, as illustrated hereinafter in Step A of Example 1, in the presence of an acid binding agent.

The compounds of the formula VI can be prepared in various ways from a variety of known materials such as nitro-substituted benzofurans and nitro-substituted 2,3-dihydro-benzofurans. In one such procedure, the compounds of the formula VI are prepared by subjecting a 2,3-dihydro-benzofuran of the formula VII:

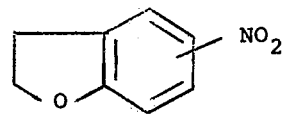

to reductive hydrogenation in the presence of a suitable catalyst such as Raney Nickel. The process is conveniently carried out at a temperature of from 0°C. to 100°C., preferably 15°C. to 40°C., and in the presence of an inert solvent of conventional type for such reaction, e.g., a lower alkanol such as ethanol.

In another procedure, the compounds of the formula VI are prepared by subjecting a compound of the formula VIII:

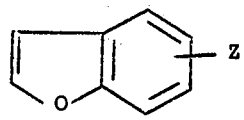

in which Z is —NO₂ or —NH₂, to catalytic hydrogenation. The process is suitably carried out at a temperature of from 0°C. to 100°C., preferably 20°C. to 50°C., and in the presence of an inert solvent of conventional type for such reactions, e.g., a lower alkanol such as ethanol. Suitable catalysts are known and include rhodium on carbon and palladium on carbon. The reaction is carried out until the required uptake of hydrogen is completed, as is conventional in such reactions.

The particular process used for the preparation of the desired compound of the formula VI will depend upon known factors including the choice and availability of starting materials. The compound of the formula VII in which the nitro substituent is in the 5- and 7- position are known and may be prepared as described by N. Rollins et al., J. Heterocycl. Chem. 5 (1), 1–6 (1968) (Eng.). All of the compounds of the formula VIII in which Z is —NO₂ are generally known, for example, from R. Andrisano et al., Gazz. Chim. ital. 86, 1257–68(1956). The compounds 5-nitrobenzofuran and 5-benzofuranamine are also known from H. Erlewmeyer et al., Helv. Chim. Acta. 31, 75–7(1948). The compounds 6-nitrobenzofuran and 6-benzofuranamine are also known from P. Rumpt et al., Helv. Chim. Acta 37, 435–6(1954). The compounds 5-nitro and 7-nitrobenzofuran are also described from A. Rao et al., Symp. Syn. Heterocycl. Compounds Physiol. Interest Hyderabad, India 1964(Pub. 1966), 26–30 (Eng.).

The compounds of formula I are useful because they possess pharmaceutical activity in animals. In particular, the compounds I are useful as anti-inflammatory agents as indicated by the Carrageenan-induced edema test in rats. For such use, the compounds may be combined with a pharmaceutically acceptable carrier, and such other conventional adjuvants as may be desired, and preferably administered orally in such forms as tablets, capsules, elixirs, suspensions and the like. For the above-mentioned use, the dosage administered will, of course, vary depending upon known factors such as the particular compound used and mode of administration. However, in general, the compounds of formula I provide satisfactory results when administered at a daily dose of from about 0.4 milligrams to 180 milligrams per kilogram of body weight, preferably given in divided doses 2 to 4 times a day, with daily dosage for large mammals ranging from between about 40 milligrams to 1000 milligrams and individual doses between 10 milligrams to 500 milligrams.

The compounds of the formula I are also useful as analgesics as indicated by application of pressure to yeast-inflammed foot of the rat (oral administration). They are also useful as anti-pyretics as indicated by inhibition of yeast-induced fever in rats (oral administration). For such uses, the compound may be administered to obtain satisfactory results in modes and forms similar to those employed in the treatment of inflammation and at dosages indicated above as applicable for the use of the compounds I in the treatment of inflammation.

For the above usage, oral administration with carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules preferably contain the active ingredient admixed with an inert solid diluent, e.g., calcium carbonate, calcium phosphate and kaolin. The preferred pharmaceutical composition from the standpoint of preparation and ease of administration are solid compositions, particularly solid diluent-filled capsules and tablets.

A representative individual dose form suitable for oral administration four times a day is a capsule prepared by conventional techniques and containing the following ingredients.

| Ingredient | Parts by Weight |
|---|---|
| Compound of Formula I, e.g. of Example 1 hereinafter | 50 |
| Inert diluent | 200 |

Prepared pharmaceutical compounds of the formula I are those in which R is isopropyl and R' is phenyl or fluorophenyl.

The following Examples illustrate the present invention.

EXAMPLE A 2,3-Dihydro-5-benzofuranamine: A mixture of 10 g. of 5-nitro-2,3-dihydrobenzofuran, 2.5 g. of Raney Nickel and 50 ml. of ethanol is hydrogenated in a Parr apparatus at a hydrogen pressure of 50 p.s.i. and room temperature until the uptake of hydrogen ceases. The resulting mixture is filtered to remove catalyst and the filtrate evaporated in vacuo to obtain an oil of 2,3-dihydro-5-benzofuranamine.

EXAMPLE B

Following the procedure of Example A there is obtained 2,3-dihydro-7-benzofuranamine on substituting 7-nitro-2,3-dihydrobenzofuran for the 5-nitro-2,3-dihydrobenzofuran of Example A.

EXAMPLE C 2,3-Dihydro-4-benzofuranamine: A mixture of 3.0 g. of 4-nitrobenzofuran, 0.5 g of 5% Rhodium on carbon and 25 ml. of ethanol is hydrogenated in a Parr apparatus at a hydrogen pressure of 50 p.s.i. and temperature of 35°C. until the uptake of hydrogen ceases. The catalyst is removed by filtration and the filtrate evaporated in vacuo to obtain an oil of 2,3-dihydro-4-benzofuranamine.

EXAMPLE D

Following the procedure of Example C but substituting 6-nitrobenzofuran for the 4-nitrobenzofuran there is obtained 2,3-dihydro-6-benzofuranamine.

EXAMPLE 1

1-Isopropyl-7,8-dihydro-4-phenyl-furo[2,3-h]quinazolin-2(1H)-one

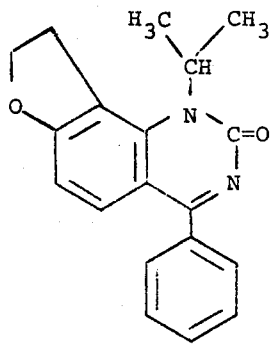

STEP A: Preparation of N-isopropyl-2,3-dihydro-4-benzofuranamine

To a solution of 19.7 g. of 2,3-dihydro-4-benzofuranamine in 150 ml. of methanol is added 11 ml. of isopropyliodide and 15.5 ml. of triethylamine. The solution is refluxed for 40 hours and then concentrated in vacuo. The resultant oil is extracted and combined, filtered through Celite, and the ether removed in vacuo to give an oil of N-isopropyl-2,3-dihydro-4-benzofuranamine.

STEP B: Preparation of 1-isopropyl-1-(2,3-dihydro-4- benzofuranyl)urea

To a solution of 7.4 g. of N-isopropyl-2,3-dihydro-4-benzofuranamine in 200 ml. of glacial acetic acid, cooled to 15°± 5°C. is added 2.5 g. of sodium isocyanate. The mixture is stirred at room temperature for 15 hours and then concentrated in vacuo. The residue is treated with 150 ml. of 2N sodium hydroxide and then extracted with chloroform. The chloroform extract is dried with anhydrous magnesium sulfate, filtered and concentrated in vacuo to give an oil of 1-isopropyl-1-(2,3-dihydro-4-benzofuranyl) urea.

STEP C: Preparation of 1-isopropyl-3,4,7,8-tetrahydro-4-phenyl-furo[2,3-h]quinazolin-2(1H)-one A solution of 5.0 g. of 1-isopropyl-1-(2,3-dihydro-4-benzofuranyl)urea, 3.5 ml. of benzaldehyde, 3 drops of methanesulfonic acid and 150 ml. of toluene is stirred and refluxed under a water separator for 20 hours. The resulting solution is cooled and the cooled solution is washed with 150 ml. water, dried with anhydrous magnesium sulfate, filtered and concentrated in vacuo to give an oil of 1-isopropyl-3,4,7,8-tetrahydro-4-phenyl-furo[2,3-h]quinazolin-2(1H)-one.

STEP D: Preparation of 1-isopropyl-7,8-dihydro-4-phenyl-furo[2,3-h]quinazolin-2(1H)-one To a stirred solution of 8.5 g. of 1-isopropyl-3,4,7,8-tetrahydro-4-phenyl-furo[2,3-h]quinazolin-2(1H)-one in 250 ml. of dioxane cooled to 8°±5°C. is added dropwise a solution of 4.3 g. of potassium permanganate in 185 ml. of water. After the addition is completed 2 ml. of formalin solution is added. The resulting precipitated solids are removed by filtration and the filtrate concentrated in vacuo to give an oil of 1-isopropyl-7,8-dihydro-4-phenyl-furo[2,3-h]quinazolin-2(1H)-one.

EXAMPLE 2

1-Isopropyl-4-phenyl-7,8-dihydro-furo[2,3-g]quinazolin-2(1H)-one and
4-isopropyl-1-phenyl-8,9-dihydro-furo[3,2-f]quinazolin-3(4H)-one

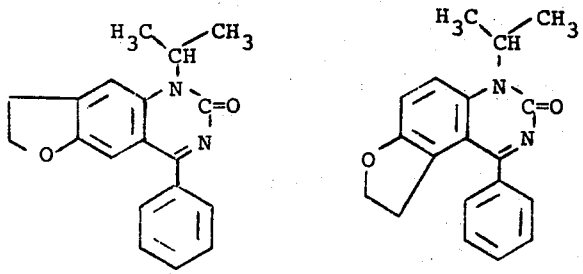

STEP A: Preparation of N-isopropyl-2,3-dihydro-5-benzofuranamine

To a solution of 40 g. of 2,3-dihydro-5-benzofuranamine in 200 ml. of methanol is added 23 ml. of isopropyl iodide and 35 ml. of triethylamine. The solution is refluxed for 55 hours and then concentrated in vacuo. The resultant oil is extracted several times with diethyl ether, the extract combined, filtered through Celite, and the ether removed in vacuo to obtain an oil of N-isopropyl-2,3-dihydro-5-benzofuranamine.

STEP B: Preparation of 1-isopropyl-1-(2,3-dihydro-5-benzofuranyl)urea

To a solution of 14.2 g. of N-isopropyl-2,3-dihydro-5-benzofuranamine in 300 ml. of glacial acetic acid, cooled to 15°±5°C. is added 4.9 g. of sodium isocyanate. The mixture is stirred at room temperature for 18 hours and then concentrated in vacuo. The residue is treated with 200 ml. of 2N sodium hydroxide solution and then extracted twice with chloroform. The combined chloroform extracts are dried with anhydrous magnesium fulfate, filtered and concentrated in vacuo to obtain an oil of 1-isopropyl-1-(2,3-dihydro-5-benzofuranyl)urea.

STEP C: Preparation of 1-isopropyl-3,4,7,8-tetrahydro-4-phenyl-furo[2,3-g]quinazolin-2(1H)-one and 4-isopropyl-1-phenyl-1,2,8,9-tetrahydro-furo[3,2-f]quinazolin-3(4H)-one A solution of 9.6 g. of 1-isopropyl-1-(2,3-dihydro-5-benzofuranyl)urea, 6.9 ml. of benzaldehyde, 6 drops of methanesulfonic acid and 200 ml. of toluene is stirred and refluxed under a water separator for 25 hours. The resulting solution is cooled, washed twice with 150 ml. of water, dried with anhydrous magnesium sulfate, filtered and concentrated in vacuo. The residue is dissolved in a minimum amount of chloroform and chromotagraphed on silica gel (200 g.) using chloroform as eluent to obtain an oil of 1-isopropyl-3,4,7,8-tetrahydro-4-phenyl-furo[2,3-g]guinazolin-2(1H)-one and an oil of 4-isopropyl-1-phenyl-1,2,8,9-tetrahydro-furo[3,2-f]quinazolin-3(4H)-one.

STEP D-1; Preparation of 1-isopropyl-7,8-dihydro-4-phenyl-furo[2,3-g]quinazolin-2(1H)-one To a stirred solution of 4.6 g. of 1-isopropyl-3,4,7,8-tetrahydro-4-phenyl-furo[2,3-g]quinazolin-2(1H)-one in 200 ml. of dioxane cooled to 5°±5°C. is added dropwise a solution of 3.0 g. of potassium permanganate in 140 ml. of water. After the addition is completed 1.5 ml. of formalin solution is added. The resulting precipitated solids are removed by filtration and the filtrate concentrated in vacuo to obtain an oil of 1-isopropyl-7,8-dihydro-4-phenyl-furo[2,3-g]quinazolin-2(1H)-one.

STEP D-2: Preparation of 4-isopropyl-1-phenyl-8,9-dihydro-furo[3,2-f]quinazolin-3(4H)-one Following the procedure of Step D-1 but replacing the 1-isopropyl-3,4,7,8-tetrahydro-4-phenyl-furo[2,3-g]quinazolin-2(1H)-one with 2.8 g. of 4-isopropyl-1-phenyl-1,2,8,9-tetrahydro-furo[3,2-f]quinazolin-3(4H)-one there is obtained an oil of 4-isopropyl-1-phenyl-8,9-dihydro-furo[3,2-f]quinazolin-3(4H)-one.

EXAMPLE 3

1-Isopropyl-4-phenyl-6,7-dihydro-furo[3,2-g]quinazolin-2(1H)-one and
6-isopropyl-9-phenyl-2,3-dihydro-furo[3,2-f]quinazolin-7(6H)-one

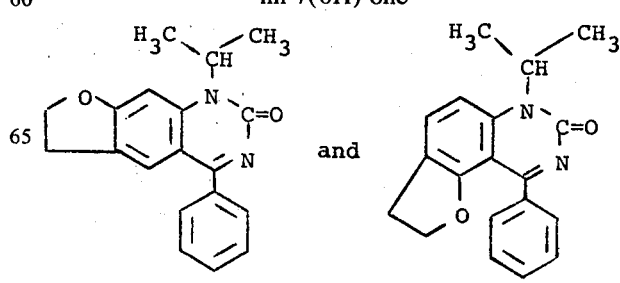

STEP A: Preparation of N-isopropyl-2,3-dihydro-6-benzofuranamine

To a solution of 2.8 g. of 2,3-dihydro-6-benzofuranamine in 150 ml. of methanol is added 18 ml. of isopropyl iodide and 26.5 ml. of triethylamine. The solution is refluxed for 60 hours and then concentrated in vacuo. The resultant oil is extracted repeatedly with diethyl ether. The extracts are combined, filtered through Celite, and the ether removed in vacuo to give an oil of N-isopropyl-2,3-dihydro-6-benzofuranamine.

STEP B: Preparation of 1-isopropyl-1-(2,3-dihydro-6-benzofuranyl)urea

To a solution of 12.2 g. of N-isopropyl-2,3-dihydro-6-benzofuranamine in 250 ml. of glacial acetic acid, cooled to 15°±5°C. is added 24.0 g. of sodium isocyanate. The mixture is stirred at room temperature for 18 hours and then concentrated in vacuo. The residue is treated with 200 ml. of 2N sodium hydroxide solution and then extracted twice with chloroform. The combined chloroform extracts are dried with anhydrous magnesium sulfate, filtered and concentrated in vacuo to obtain an oil of 1-isopropyl-1-(2,3-dihydro-6-benzofuranyl)urea.

STEP C: Preparation of 1-isopropyl-3,4,6,7-tetrahydro-4-phenyl-furo[3,2g]quinazolin-2(1H)-one and 6-isopropyl-9-phenyl-2,3,8,9-tetrahydro-furo[2,3-f]quinazolin-7(6H)-one A solution of 8.0 g. of 1-Isopropyl-1-(2,3-dihydro-6-benzofuranyl)urea, 3.6 ml. of benzaldehyde, 5 drops of methanesulfonic acid and 200 ml. of toluene is stirred and refluxed under a water separator for 20 hours. The resulting solution is cooled and the cooled solution is washed twice with 150 ml. water, dried with anhydrous magnesium sulfate, filtered and concentrated in vacuo. The residue is dissolved in a minimum amount of chloroform and chromatographed on silica gel (200 g.) using chloroform as an eluent to give an oil of 1-isopropyl-4-phenyl-3,4,6,7-tetrahydro-furo[3,2-g] quinazolin-2(1H)-one and an oil of 6-isopropyl -9-phenyl-2,3,8,9-tetrahydro-furan[2,3-f]quinazolin-7(6H)-one.

STEP D-1: Preparation of 1-isopropyl-6,7-dihydro-4-phenyl-furo[3,2-g]quinazolin-2(1H)-one To a stirred solution of 3.2 g. of 1-isopropyl-3,4,6,7-tetrahydro-4-phenyl-furo[3,2-g]quinazolin-2(1H)-one in 150 ml. of dioxane cooled to 8°±5°C. is added dropwise a solution of 2.0 g. of potassium permanganate in 130 ml. of water. After the addition is completed 1.5 ml. of formalin solution is added. The resulting precipitated solids are removed by filtration and the filtrate concentrated in vacuo to give an oil of 1-isopropyl-6,7-dihydro-4-phenyl-furo[3,2-g]quinazolin-2(1H)-one.

STEP D-2: Preparation of 6-isopropyl-9-phenyl-2,3-dihydro-furo[2,3-f]quinazolin-7(6H)-one Following the procedure of Step D-1 of this example but replacing the 1-isopropyl-3,4,6,7-tetrahydro-4-phenyl-furo[3,2-g]quinazolin-2(1H)-one with 2.1 g. of 6-isopropyl-9-phenyl-2,3,8,9-tetrahydro-furo[2,3-f]quinazolin-7(6H)-one, there is obtained an oil of 6-isopropyl-9-phenyl-2,3-dihydro-furo[2,3-f]quinazolin-7(6H)-one.

EXAMPLE 4

1-Isopropyl-4-phenyl-7,8-dihydro-furo[3,2-h]quinazolin-2(1H)-one

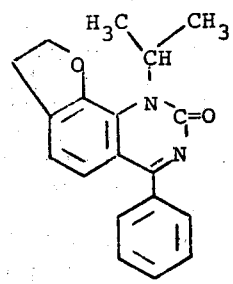

STEP A: Preparation of N-isopropyl-2,3-dihydro-7-benzofuranamine

To a solution of 15 g. of 2,3-dihydro-7-benzofuranamine in 150 ml. of methanol is added 8.5 ml. of isopropyl iodide and 13.4 ml. of triethylamine. The solution is refluxed for 45 hours and then concentrated in vacuo. The resulting oil is extracted several times with diethyl ether, the ether extracted combined filtered through Celite, and the ether removed in vacuo to obtain an oil of N-isopropyl-2,3-dihydro-7-benzofuranamine.

STEP B: Preparation of 1-isopropyl-1-(2,3-dihydro-7-benzofuranyl)urea

To a solution of 8.2 g of N-isopropyl-2,3-dihydro-7-enzofuranamine in 200 ml. of glacial acetic acid, cooled to 15°±5°C. is added 2.9 g. of sodium isocyanate. The mixture is stirred overnight at room temperature, concentrated in vacuo, the residue treated with 150 ml. of 2N sodium hydroxide solution and then extracted with chloroform. The chloroform extract is dried with anhydrous magnesium sulfate, filtered and concentrated in vacuo to give an oil of 1-isopropyl-1-(2,3-dihydro-7-benzofuranyl)urea.

STEP C: Preparation of 1-isopropyl-3,4,7,8-tetrahydro-4-phenyl-furo[3,2-h]quinazolin-2(1H)-one A solution of 4.8 g. of 1-isopropyl-1-(2,3-dihydro-7-benzofuranyl)urea, 3.4 ml of benzaldehyde, 3 drops of methanesulfonic acid and 150 ml. of toluene is stirred and refluxed under a water separator for 18 hours. The cooled solution is washed with 150 ml. of water, dried with anhydrous magnesium sulfate, filtered and concentrated in vacuo to give an oil of 1-isopropyl-3,4,7,8-tetrahydro-4-phenyl-furo[3,2-h]quinazolin-2(1H)-one.

STEP D: Preparation of 1-isopropyl-7,8-dihydro-4-phenyl-furo[3,2-h]quinazolin-2(1H)-one To a stirred solution of 4.2 g. of 1-isopropyl-3,4,7,8-tetrahydro-4-phenyl-furo[3,2-h]quinazolin-2(1H)-one in 180 ml. of dioxane cooled to 8°±5°C. is added dropwise a solution of 2.3 g. of potassium permanganate in 100 ml. of water. After the addition is completed 1.5 ml. of formalin solution is added. The solids which precipitate are removed by filtration and the filtrate concentrated in vacuo to obtain an oil of 1-isopropyl-7,8-dihydro-4-phenyl-furo[3,2-h]quinazolin-2(1H)-one.

EXAMPLE 5

Part A: Following the procedure of Step A of Example 1 there is prepared:
1. N-methallyl-2,3-dihydro-4-benzofuranamine.
2. N-t-butyl-2,3-dihydro-4-benzofuranamine.
3. N-cyclopropylmethyl-2,3-dihydro-4-benzofuranamine.

Part B: Following the procedure of Step B of Example 1 there is prepared:
1. 1-methallyl-1-(2,3-dihydro-4-benzofuranyl)urea.
2. 1-t-butyl-1-(2,3-dihydro-4-benzofuranyl)urea.

3. 1-cyclopropylmethyl-1-(2,3-dihydro-4-benzofuranyl)urea.

Part C: Following the procedure of Step C of Example 1 there is prepared:
1. 1-methallyl-3,4,7,8-tetrahydro-4-phenyl-furo[2,3-h]quinazolin-2(1H)-one.
2. 1-t-butyl-3,4,7,8-tetrahydro-4-phenyl-furo[2,3-h]quinazolin-2(1H)-one.
3. 1-cyclopropylmethyl-3,4,7,8-tetrahydro-4-phenyl-furo[2,3-h]quinazolin-2(1H)-one.
4. 1-isopropyl-3,4,7,8-tetrahydro-4-p-fluorophenyl-furo[2,3-h]quinazolin-2(1H)-one.

Part D: Following the procedure of Step D of Example 1 there is prepared:
1. 1-methallyl-7,8-dihydro-4-phenyl-furo[2,3-h]quinazolin-2(1H)-one, as an oil.
2. 1-t-butyl-7,8-dihydro-4-phenyl-furo[2,3-h]quinazolin-2(1H)-one, as an oil.
3. 1-cyclopropylmethyl-7,8-dihydro-4-phenyl-furo[2,3-h]quinazolin-2(1H)-one, as an oil.
4. 1-isopropyl-7,8-dihydro-4-p-fluorophenyl-furo[2,3-h]quinazolin-2(1H)-one, as an oil.

EXAMPLE 6

Part A: Following the procedure of Step A of Example 2 there is prepared:
1. N-t-butyl-2,3-dihydro-5-benzofuranamine.
2. N-cyclopropylmethyl-2,3-dihydro-5-benzofuranamine.

Part B: Following the procedure of Step B of Example 2 there is prepared:
1. 1-t-butyl-1-(2,3-dihydro-5-benzofuranyl)urea.
2. 1-cyclopropylmethyl-1-(2,3-dihydro-5-benzofuranyl)urea.

Part C: Following the procedure of Step C of Example 2 there is prepared:
1a. 1-t-butyl-3,4,7,8-tetrahydro-4-phenyl-furo[2,3-g]quinazolin-2(1H)-one.
1b. 4-t-butyl-1-phenyl-1,2,8,9-tetrahydro-furo[3,2-f]quinazolin-3(4H)-one.
2a. 1-cyclopropylmethyl-3,4,7,8-tetrahydro-4-phenyl-furo[2,3-g]quinazolin-2(1H)-one.
2b. 4-cyclopropylmethyl-1-phenyl-1,2,8,9-tetrahydro-furo[3,2-f]quinazolin-3(4H)-one.
3a. 1-isopropyl-3,4,7,8-tetrahydro-4-p-fluorophenyl-furo[2,3-g]quinazolin-2(1H)-one.
3b. 4-isopropyl-1-p-fluorophenyl-1,2,8,9-tetrahydro-furo[3,2-f]quinazolin-3(4H)-one.

Part D: Following the procedure of Steps D-1 and D-2 of Example 2 there is prepared:
1a. 1-t-butyl-7,8-dihydro-4-phenyl-furo[2,3-g]quinazolin-2(1H)-one, as an oil.
1b. 4-t-butyl-1-phenyl-8,9-dihydro-furo[3,2-f]quinazolin-3(4H)-one, as an oil.
2a. 1-cyclopropylmethyl-7,8-dihydro-4-phenyl-furo[2,3-g]quinazolin-2(1H)-one, as an oil.
2b. 4-cyclopropylmethyl-1-phenyl-8,9-dihydro-furo[3,2-f]quinazolin-3(4H)-one, as an oil.
3a. 1-isopropyl-7,8-dihydro-4-p-fluorophenyl-furo[2,3-g]quinazolin-2(1H)-one, as an oil.
3b. 4-isopropyl-1-p-fluorophenyl-8,9-dihydro-furo[3,2-f]quinazolin-3(4H)-one, as an oil.

EXAMPLE 7

Part A: Following the procedure of Step A of Example 3 there is prepared:
1. N-methallyl-2,3-dihydro-6-benzofuranamine.
2. N-t-butyl-2,3-dihydro-6-benzofuranamine.
3. N-cyclopropylmethyl-2,3-dihydro-6-benzofuranamine.
4. N-cyclopentylmethyl-2,3-dihydro-6-benzofuranamine.

Part B: Following the procedure of Step B of Example 3 there is prepared:
1. 1-methallyl-1-(2,3-dihydro-6-benzofuranyl)urea.
2. 1-t-butyl-1-(2,3-dihydro-6-benzofuranyl)urea.
3. 1-cyclopropylmethyl-1-(2,3-dihydro-6-benzofuranyl)urea.
4. 1-cyclopentylmethyl-1-(2,3-dihydro-6-benzofuranyl)urea.
5. 1-ethyl-1-(2,3-dihydro-6-benzofuranyl)urea (on separation from 1,1-diethyl-1-(2,3-dihydro-6-benzofuranyl)urea which is also formed during the preparation).

Part C: Following the procedure of Step C of Example 3 there is prepared:
1a. 1-methallyl-3,4,6,7-tetrahydro-4-phenyl-furo[3,2-g]quinazolin-2(1H)-one, as an oil.
1b. 6-methallyl-9-phenyl-2,3,8,9-tetrahydro-furo[2,3-f]quinazolin-7(6H)-one, as an oil.
2a. 1-t-butyl-3,4,6,7-tetrahydro-4-phenyl-furo[3,2-g]quinazolin-2(1H)-one, as an oil.
2b. 6-t-butyl-9-phenyl-2,3,8,9-tetrahydro-furo[2,3-f]quinazolin-7(6H)-one, as an oil.
3a. 1-cyclopropylmethyl-3,4,6,7-tetrahydro-4-phenyl-furo[3,2-g]quinazolin-2(1H)-one, as an oil.
3b. 6-cyclopropylmethyl-9-phenyl-2,3,8,9-tetrahydro-furo[2,3-f]quinazolin-7(6H)-one, as an oil.
4a. 1-cyclopentylmethyl-3,4,6,7-tetrahydro-4-phenyl-furo[3,2-g]quinazolin-2(1H)-one, as an oil.
4b. 6-cyclopentylmethyl-9-phenyl-2,3,8,9-tetrahydro-furo[2,3-f]quinazolin-7(6H)-one, as an oil.
5a. 1-ethyl-3,4,6,7-tetrahydro-4-phenyl-furo[3,2-g]quinazolin-2(1H)-one, as an oil.
5b. 6-ethyl-9-phenyl-2,3,8,9-tetrahydro-furo[2,3-f]quinazolin-7(6H)-one, as an oil.
6a. 1-isopropyl-3,4,6,7-tetrahydro-4-(p-methylphenyl)-furo[3,2-g]quinazolin-2(1H)-one, as an oil.
6b. 6-isopropyl-9-(p-methylphenyl)-2,3,8,9-tetrahydro-furo[2,3-f]quinazolin-7(6H)-one, as an oil.
7a. 1-isopropyl-3,4,6,7-tetrahydro-4-(p-fluorophenyl)-furo[3,2-g]quinazolin-2(1H)-one, as an oil.
7b. 6-isopropyl-9-(p-fluorophenyl)-2,3,8,9-tetrahydro-furo[2,3-f]quinazolin-7(6H)-one, as an oil.
8a. 1-isopropyl-3,4,6,7-tetrahydro-4-(p-trifluoromethylphenyl)-furo[3,2-g]quinazolin-2(1H)-one, as an oil.
8b. 6-isopropyl-9-(p-trifluoromethylphenyl)-2,3,8,9-tetrahydro-furo[2,3-f]quinazolin-7(6H)-one, as an oil.
9a. 1-isopropyl-3,4,6,7-tetrahydro-4-(m-methoxyphenyl)-furo[3,2-g]quinazolin-2(1H)-one, as an oil.
9b. 6-isopropyl-9-(m-methoxyphenyl)-2,3,8,9-tetrahydro-furo[2,3-f]quinazolin-7(6H)-one, as an oil.

Part D: Following the procedure of Step D of Example 3 there is prepared:
1a. 1-methallyl-6,7-dihydro-4-phenyl-furo[3,2-g]quinazolin-2(1H)-one, as an oil.
1b. 6-methallyl-9-phenyl-2,3-dihydro-furo[2,3-f]quinazolin-7(6H)-one, as an oil.
2a. 1-t-butyl-6,7-dihydro-4-phenyl-furo[3,2-g]quinazolin-2(1H)-one, as an oil.

2b. 6-t-butyl-9-phenyl-2,3-dihydro-furo[2,3-f]quinazolin-7(6H)-one, as an oil.
3a. 1-cyclopropylmethyl-6,7-dihydro-4-phenyl-furo[3,2-g]quinazolin-2(1H)-one, as an oil.
3b. 6-cyclopropylmethyl-9-phenyl-2,3-dihydro-furo[2,3-f]quinazolin-7(6H)-one, as an oil.
4a. 1-cyclopentylmethyl-6,7-dihydro-4-phenyl-furo[3,2-g]quinazolin-2(1H)-one, as an oil.
4b. 6-cyclopentylmethyl-9-phenyl-2,3-dihydro-furo[2,3-f]quinazolin-7(6H)-one, as an oil.
5a. 1-ethyl-6,7-dihydro-4-phenyl-furo[3,2-g]quinazolin-2(1H)-one, as an oil.
5b. 6-ethyl-9-phenyl-2,3-dihydro-furo[2,3-f]quinazolin-7(6H)-one, as an oil.
6a. 1-isopropyl-6,7-dihydro-4-(p-methylphenyl)-furo[3,2-g]quinazolin-2(1H)-one, as an oil.
6b. 6-isopropyl-9-(p-methylphenyl)-2,3-dihydro-furo[2,3-f]quinazolin-7(6H)-one, as an oil.
7a. 1-isopropyl-6,7-dihydro-4-(p-fluorophenyl-furo[3,2-g]quinazolin-2(1H)-one, as an oil.
7b. 6-isopropyl-9-(p-fluorophenyl)-2,3-dihydro-furo[2,3-f]quinazolin-7(6H)-one, as an oil.
8a. 1-isopropyl-6,7-dihydro-4-(p-trifluoromethylphenyl)-furo[3,2-g]quinazolin-2(1H)-one, as an oil.
8b. 6-isopropyl-9-(p-trifluoromethylphenyl)-2,3-dihydro-furo[2,3-f]quinazolin-7(6H)-one, as an oil.
9a. 1-isopropyl-6,7-dihydro-4-(m-methoxyphenyl)-furo[3,2-g]quinazolin-2(1H)-one, as an oil.
9b. 6-isopropyl-9-(m-methoxyphenyl)-2,3-dihydro-furo[2,3-f]quinazolin-7(6H)-one, as an oil.

EXAMPLE 8

Part A: Following the procedure of Step A of Example 4 there is prepared:
1. N-methallyl-2,3-dihydro-7-benzofuranamine.
2. N-t-butyl-2,3-dihydro-7-benzofuranamine.
3. N-cyclopropylmethyl-2,3-dihydro-7-benzofuranamine.

Part B: Following the procedure of Step B of Example 4 there is prepared:
1. 1-methallyl-1-(2,3-dihydro-7-benzofuranyl)urea.
2. 1-t-butyl-1-(2,3-dihydro-7-benzofuranyl)urea.
3. 1-cyclopropylmethyl-1-(2,3-dihydro-7-benzofuranyl)urea.

Part C: Following the procedure of Step C of Example 4 there is prepared:
1. 1-methallyl-3,4,7,8-tetrahydro-4-phenyl-furo[3,2-h]quinazolin-2(1H)-one.
2. 1-t-butyl-3,4,7,8-tetrahydro-4-phenyl-furo[3,2-h]quinazolin-2(1H)-one.
3. 1-cyclopropylmethyl-3,4,7,8-tetrahydro-4-phenyl-furo[3,2-h]quinazolin-2(1H)-one.
4. 1-isopropyl-3,4,7,8-tetrahydro-4-p-fluorophenyl-furo[3,2-h]quinazolin-2(1H)-one.

Part D: Following the procedure of Step D of Example 4 there is prepared:
1. 1-methallyl-3,4,7,8-tetrahydro-4-phenyl-furo[3,2-h]quinazolin-2(1H)-one, as an oil.
2. 1-t-butyl-3,4,7,8-tetrahydro-4-phenyl-furo[3,2-h]quinazolin-2(1H)-one, as an oil.
3. 1-cyclopropylmethyl-3,4,7,8-tetrahydro-4-phenyl-furo[3,2-h]quinazolin-2(1H)-one, as an oil.
4. 1-isopropyl-3,4,7,8-tetrahydro-p-fluorophenyl-furo[3,2-h]quinazolin-2(1H)-one, as an oil.

What is claimed is:
1. A compound of the formula:

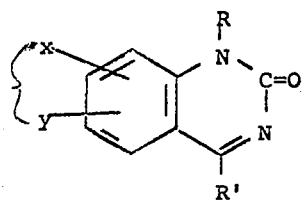

wherein $\widehat{xy}$ is —OCH$_2$CH$_2$— or —CH$_2$CH$_2$O—,
R is alkyl of 1 to 6 carbon atoms, allyl, methallyl or cycloalkylalkyl of 4 to 8 carbon atoms in which the cycloalkyl portion is of 3 to 6 carbon atoms and the alkyl portion is of 1 to 2 carbon atoms,
R' is

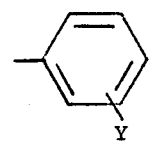

Y is hydrogen, fluoro, chloro, alkyl of 1 to 4 carbon atoms, alkoxy of 1 to 4 carbon atoms or trifluoromethyl.
2. A compound of claim 1 in which R is alkyl.
3. A compound of claim 1 in which R is isopropyl.
4. A compound of claim 1 in which R' is phenyl or fluorophenyl.
5. A compound of claim 3 in which R' is phenyl or fluorophenyl.
6. A compound of claim 1 in which R is cyclopropylmethyl.
7. A compound of claim 1 of the formula:

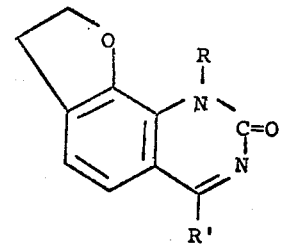

in which R and R' are as defined in claim 1.
8. A compound of claim 7 in which R is alkyl.
9. A compound of claim 7 in which R is isopropyl.
10. A compound of claim 7 in which R' is phenyl or fluorophenyl.
11. A compound of claim 9 in which R' is phenyl or fluorophenyl.
12. A compound of claim 7 in which R is cyclopropylmethyl.
13. The compound of claim 11 in which R' is phenyl.
14. The compound of claim 11 in which R' is p-fluorophenyl.
15. The compound of claim 12 in which R' is phenyl.
16. The compound of claim 8 in which R is t-butyl and R' is phenyl.
17. The compound of claim 8 in which R is methyl and R' is phenyl.
18. A compound of claim 1 of the formula:

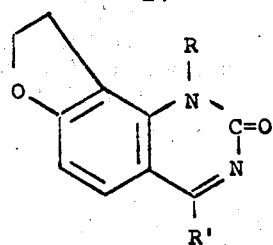

wherein R and R' are as defined in claim 1.

19. A compound of claim 18 in which R is alkyl.
20. A compound of claim 18 in which R is isopropyl.
21. A compound of claim 18 in which R' is phenyl or fluorophenyl.
22. A compound of claim 20 in which R' is phenyl or fluorophenyl.
23. A compound of claim 18 in which R is cyclopropylmethyl.
24. The compound of claim 22 in which R' is phenyl.
25. The compound of claim 22 in which R' is p-fluorophenyl.
26. The compound of claim 23 in which R' is phenyl.
27. The compound of claim 18 in which R is t-butyl and R' is phenyl.
28. The compound of claim 18 in which R is methyl and R' is phenyl.
29. A compound of claim 1 of the formula:

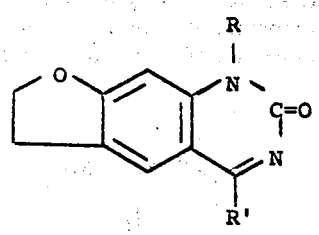

in which R and R' are as defined in claim 1.

30. A compound of claim 29 in which R is alkyl.
31. A compound of claim 29 in which R is isopropyl.
32. A compound of claim 29 in which R' is phenyl or fluorophenyl.
33. A compound of claim 31 in which R' is phenyl or fluorophenyl.
34. A compound of claim 29 in which R is cyclopropylmethyl.
35. The compound of claim 33 in which R' is phenyl.
36. The compound of claim 33 in which R' is p-fluorophenyl.
37. The compound of claim 34 in which R' is phenyl.
38. The compound of claim 29 in which R is t-butyl and R' is phenyl.
39. The compound of claim 29 in which R is methyl and R' is phenyl.
40. A compound of claim 1 of the formula:

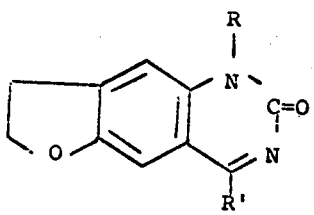

in which R and R' are as defined in claim 1.

41. A compound of claim 40 in which R is alkyl.
42. A compound of claim 40 in which R is isopropyl.
43. A compound of claim 40 in which R' is phenyl or fluorophenyl.
44. A compound of claim 42 in which R' is phenyl or fluorophenyl.
45. A compound of claim 40 in which R is cyclopropylmethyl.
46. The compound of claim 44 in which R' is phenyl.
47. The compound of claim 44 in which R' is p-fluorophenyl.
48. The compound of claim 45 in which R' is phenyl.
49. The compound of claim 40 in which R is t-butyl and R' is phenyl.
50. The compound of claim 40 in which R is methyl and R' is phenyl.
51. A compound of claim 1 of the formula:

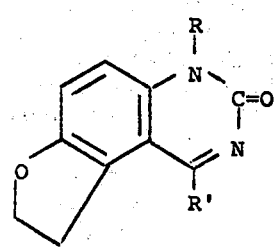

in which R and R' are as defined in claim 1.

52. A compound of claim 51 in which R is alkyl.
53. A compound of claim 51 in which R is isopropyl.
54. A compound of claim 51 in which R' is phenyl or fluorophenyl.
55. A compound of claim 53 in which R' is phenyl or fluorophenyl.
56. A compound of claim 51 in which R is cyclopropylmethyl.
57. The compound of claim 55 in which R' is phenyl.
58. The compound of claim 55 in which R' is p-fluorophenyl.
59. The compound of claim 56 in which R' is phenyl.
60. The compound of claim 51 in which R is t-butyl and R' is phenyl.
61. The compound of claim 51 in which R is methyl and R' is phenyl.
62. A compound of claim 1 of the formula:

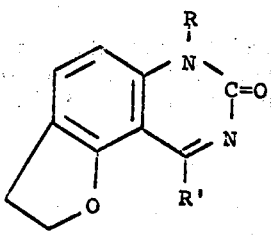

in which R and R' are as defined in claim 1.

63. A compound of claim 62 in which R is alkyl.
64. A compound of claim 62 in which R is isopropyl.
65. A compound of claim 62 in which R' is phenyl or fluorophenyl.
66. A compound of claim 64 in which R' is phenyl or fluorophenyl.
67. A compound of claim 62 in which R is cyclopropylmethyl.
68. The compound of claim 66 in which R' is phenyl.
69. The compound of claim 66 in which R' is p-fluorophenyl.
70. The compound of claim 67 in which R' is phenyl.

71. The compound of claim 62 in which R is t-butyl and R' is phenyl.

72. The compound of claim 62 in which R is methyl and R' is phenyl.

73. A compound of the formula:

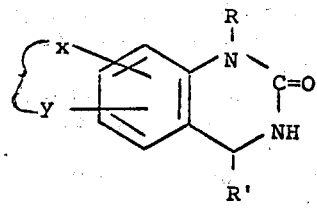

wherein $\overset{\frown}{x\ y}$ is —OCH$_2$CH$_2$— or —CH$_2$CH$_2$O,

R is alkyl of 1 to 6 carbon atoms, allyl, methallyl or cycloalkylalkyl of 4 to 8 carbon atoms in which the cycloalkyl portion is of 3 to 6 carbon atoms and the alkyl portion is of 1 to 2 carbon atoms, R' is

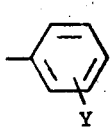

and

Y is hydrogen, fluoro, chloro, alkyl of 1 to 4 carbon atoms, alkoxy of 1 to 4 carbon atoms or trifluoromethyl.

74. A compound of claim 73 in which R is alkyl.

75. A compound of claim 73 in which R is isopropyl.

76. A compound of claim 73 in which R is phenyl or fluorophenyl.

77. A compound of claim 73 of the formula:

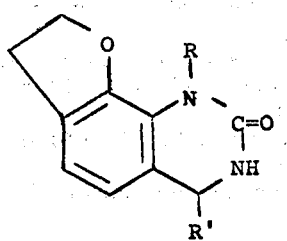

in which R and R' are as defined in claim 73.

78. A compound of claim 77 in which R is alkyl.

79. A compound of claim 73 of the formula:

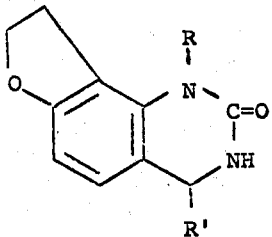

in which R and R' are as defined in claim 73.

80. A compound of claim 79 in which R is alkyl.

81. A compound of claim 73 of the formula:

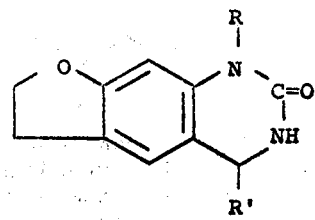

in which R and R' are as defined in claim 73.

82. A compound of claim 81 in which R is alkyl.

83. A compound of claim 73 of the formula:

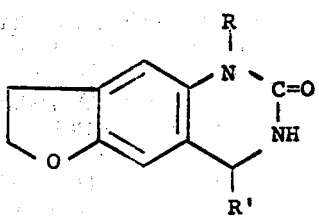

in which R and R' are as defined in claim 73.

84. A compound of claim 83 in which R is alkyl.

85. A compound of claim 73 of the formula:

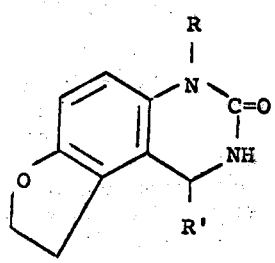

in which R and R' are as defined in claim 73.

86. A compound of claim 85 in which R is alkyl.

87. A compound of claim 73 of the formula:

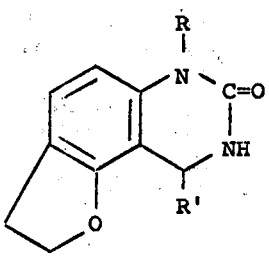

in which R and R' are as defined in claim 73.

88. A compound of claim 87 in which R is alkyl.

* * * * *